(12) United States Patent
Kaushik et al.

(10) Patent No.: US 7,196,185 B2
(45) Date of Patent: Mar. 27, 2007

(54) BOVINE GERMLINE D-GENES AND THEIR APPLICATION

(76) Inventors: Azad Kumar Kaushik, 9 Currie Drive, Morriston, Ontario (CA) N0B 2C0; Surinder Singh Saini, 78 College Avenue West, Apt. #46, Guelph, Ontario (CA) N1G 4S7; Farbod Shojaei, 227 Riverside Drive, London, Ontario (CA) N6H 1E7

( * ) Notice: Subject to any disclaimer, the term of this patent is extended or adjusted under 35 U.S.C. 154(b) by 517 days.

(21) Appl. No.: 10/429,979

(22) Filed: May 6, 2003

(65) Prior Publication Data

US 2003/0224433 A1    Dec. 4, 2003

Related U.S. Application Data

(63) Continuation-in-part of application No. 10/125,594, filed on Apr. 19, 2002, now Pat. No. 6,740,747.

(60) Provisional application No. 60/284,899, filed on Apr. 20, 2001.

(51) Int. Cl.
*C07H 21/04* (2006.01)
*C12N 15/74* (2006.01)

(52) U.S. Cl. .................. 536/23.1; 435/320.1

(58) Field of Classification Search ............ None
See application file for complete search history.

(56) References Cited

OTHER PUBLICATIONS

Saini, S.S. 1999. Molecular immunogenetics of bovine antibody. Ph D Thesis, University of Guelph.
Shojaei, F. 2001. Molecular aspects of bovine DH genes. MSc Thesis, University of Guelph.
Saini, S.S., Allore B., Jacobs, R.M. and Kaushik, A. 1999. Exceptionally long CDR3H region with multiple cysteine residues in functional bovine IgM antibodies. European Journal of Immunology. 29: 2420-26.
Saini, S.S. and Kaushik, A. 2002. Extensive CDR3H length heterogeneity exists in bovine foetal VDJ rearrangements. Scandinavian Journal of Immunology. 55:140-48.

*Primary Examiner*—Sumesh Kaushal
*Assistant Examiner*—David A. Montanari
(74) *Attorney, Agent, or Firm*—Bereskin & Parr; Micheline Gravelle (57) ABSTRACT

The present invention relates to a bovine VDJ cassette (BF1H1) that provides the novel ability to develop chimeric immunoglobulin molecule capable of incorporating both linear T cell epitope(s) (CDR1H and CDR2H) as well as conformational B cell epitope(s) (exceptionally long CDR3H). Further, multiple epitopes can be incorporated for development of multivalent vaccine by replacing at least a portion of an immunoglobulin molecule with the desired epitope such that functional ability of both epitope(s) and parent VDJ rearrangement is retained. The antigenized immunoglobulin incorporating both T and B epitopes of interest is especially useful for development of oral vaccines for use in humans apart from other species including cattle. The long CDR3H in BF1H1 VDJ rearrangement originates from long germline D-genes. The novel bovine germline D-genes provide unique molecular genetic marker for sustaining the D-gene pool in cattle essential for immunocompetence via selective breeding. D-gene specific DNA probe permits typing and selection of breeding cattle stock for maximum gemline D gene pool for better health and disease prevention. The bovine D-genes are unique to cattle and, therefore, provide sensitive and specific forensic analytical tool using molecular biology techniques to determine tissues suspected of bovine origin.

6 Claims, 5 Drawing Sheets

FIGURE 1

```
AGCTCGAGATGAACCCACTGTGGACCCTCCTCTTTGTGCTCTCAGCCCCCAGAGGGGTCCTGTCCCAGGTG
CAGCTGCGGGAGTCGGGCCCCAGCCTGGTGAAGCCGTCACAGACCCTCTCGCTCACCTGCACGGCCTCTG
GATTCTCATTGAGCGACAAGGCTGTAGGCTGGGTCCGCCAGGCTCCAGGGAAGGCGCTGGAGTGGCTCG
GTGGTATAGACACTGGTGGAAGCACAGGCTATAACCCAGGCCTGAAATCCCGGCTCAGCATCACCAAGGA
CAACTCCAAGAGCCAAGTCTCTCTGTCAGTGAGCAGCGTGACAACTGAGGACTCGGCCACATACTACTGTA
CTACTGTGCACCCCAGTCCTGATGGTTATAGTTATGGTTATGGTTGTGGTTATGGTTATGGTTGTAGTGGTT
ATGATTGTTATGGTTATGGTGGTTATGGTTATGGTGGTTATAGTAGTTATAGTTATAGTTATA
GTCCAGGAAATACTACGTCGATGCCTGGGGCCAAGGACTCCTGGTCACCGTCTCCTCAGAAGGTAATCACA
CCCGAGAGTCTTCACTAGTCT
``` pBF1H1-24
recombinant
plasmid*

EcoR I

*ZeroBlunt Vector from Invitrogen

Underlined sequence indicates BF1H1 VDJ recombination

GGGTTTCTGATGCCGGCTGTGTCACGGTGGTAGTTGTCCTGATGGTTATAGTTATGGTTATGGTTGTGGTTATGGTTATGGTT
GTAGTGGTTATGATTGTTATGGTTATGGTGGTTATGGTGGTTATGGTGGTTATGGTTATAGTAGTTATAGTTATAGTTATACT
TACGAATATACCACAGTGATACTCTCTGGGACAAAAACC

D-2 (58 bp)*

GGGTTTCTGATGCCGGCTGTGTCACGGTGGTAGTTGTTATAGTGGTTATGGTTATGGTT
GTGGTTATGGTTATGGTTATGATTATACCACAGTGACACTCTCTGGGACAAAAACC

D-3 (42 bp)*

GGGTTTCTGATGCCGGCTGTGTTGTGGTGATGATACGATAGGTGTGGTTCTAGTTATTGTAGTGTTGCTACCACAGTGATGCT
CTCAGTCTCAGAAACC

*New Classification as shown in figure 5:

D-1: DH2 as shown in figure 5 (148 bp)

D-2: DH3 as shown in figure 5 (58 bp)

D-3: DH1 as shown in figure 5 (42 bp)

```
1     GCGTGGCCACCCACCACCCCACAGGTCAGCCTGGGGAGCTCAAGACGGACTGGCGTCCCTACCTG      65
66    CCAGGTTCCTGTGCAGGATGCTGTCCACGGCCGCAATGCTTTGGCCTCTGCTCAGCTTCTGAGGT     130
131   TCTCCGGCCCACCACCACTGACCTGAATGGGCTTGGAGTGCAGGCCCAGCTGAACATCAGACCTG     195
196   GGCTCAGAGAGCCACTCGGTCCAGGGTGCACTCAGCCGTGCACCTGGAGGAGGGTCCTCCATGCC     260
261   GCAGGGTTGGCTGGGCAAGGAGGCATCACAGACCACCCTGCTGTTGGGACGTCCAGCCCTGGACC     325
326   AGGACTAGGTTCTCAGAATCCTCCCCACCACGGGACCTGTCCATACCTGGACCAGCTGACAGCTC     390
391   CCAAGGGCTCCAACCCAGCAGACAAGACCAAGGGCGCTGAAGGCGAGCAGCTAGGGTTTCTGATG     455
456   CCGGCTGTGTTGTGGTGATGATACGATAGGTGTGGTTGTAGTTATTGTAGTGTTGCTACCACAGT     520
521   GATGCTCTCAGTCTCAGAAACCCCTGCCCCGAGGTCCCAGACCAGGGAGCCTGTCCTCCAGGTAC    585
586   GCGGCACCGCCCTGCCCTCGTGACCATCAGACTGCACCCTGCACGCCCTCACCCTGCTGTCTCAG     650
651   GGCAGCAACAGCCTCTGGAGGAGTCCTGGGCCAGGCACTCGGCTGTGGAGTCCCAGACAATGATA     715
716   GCCTCAGCAGTTTCCAGCCACCTGACCCTGGAGGAGCTTGTGCAAGCTGGAGGCCGGCTGGGGCC     780
781   CGGAGCCTCAGAACCCTCCCTGCCAGGGGGCCCGTCCAGACCTGGACCAGCTGACAGCTCCCGAG     845
846   GACTGCACGCCCACCAGACGAGACCAAGGGGGCGCTGAAGGCCAGCAGCTGGGGTTTCTGATGCC     910
911   GGCTGTGTCACGGTGGTAGTTGTCCTGATGGTTATAGTTATGGTTATGGTTGTGGTTATGGTTAT    975
976   GGTTGTAGTGGTTATGATTGTTATGGTTATGGTGGTTATGGTGGTTATGGTGGTTATGGTTATAG   1040
1041  TAGTTATAGTTATAGTTATACTTACGAATATACCACAGTGATACTCTCTGGGACAAAAACCCCTG   1105
1106  CCCCTGAGGGTCCACGGCCAGGGATCCTGGAGGCTGTGTTTGGGGCACGCCCTGCCCTCCTGCCA   1170
1171  TTGGACTACAACCTGCACGCCCTCACCCTGCTGACTCGGGCAGCAACAGCTTAAGATAAGAGTCC   1235
1236  TGGGCCAGGCGCTGGGCTGTGGATACCCAGACAATGAGATCTCCAGCAGGTTCCCACCTCCTGAC   1300
1301  CCTGGAGGAACTTCCGCAGCCCTGTGGCAGGCTGGGGACCGACCCTAAGAACCCTCCCCCCGCAG   1365
1366  GGCCCGTCCAGACCTGAACCAGCTGACAGCTCCCGAGGGCTCCACGCCCCCAGACGAGACCAAG   1430
1431  GGCGGCGCCGAAGGCCAGCAGCTGGGGTTTCGATGCCGGCTGTGTCACGGTGGTAGTTGTTATAGT   1495
1496  GGTTATGGTTATGGTTGTGGTTATGGTTATGGTTATGGTTATGATTATACCACAGTGACACTCTCTGGGAC   1560
1561  AAAAACCCCTGCCCCTGAGGGTCCACGGCCAGGGATCCTGTAGGCTGTGTTTGGGGCACCGCCCT   1625
1626  GCCCTCCTGACCATCGGACTGCACCCTGCACGCCCTCACCGGGCTGTCTCAGGGCAGCAAGAGCC   1690
1691  TCAGGAAGGAGTCGCTGGGCCAGGAGCTGGGCTGCGGAGACCCAGACAGGAGACCCTCAGCAGCT   1755
1756  CCCGCCCCTGACTCTGCAGGAACTTGTGCAGGCCTGAGGCAGGCTGGGCTTCTGCTGGGACGCCA   1820
1821  TGGTCTCAGCCACCCATATCGACGGCCACAGGCGGGCAGTGGGCCAGGATCAGACTCAAAGGCCC   1885
1886  ACACTTCCCGGTCCTGTCCTGCCCGGCAGCCCAACCTGGTCACAGAGGTCCCAGGCCTGTGGCCC   1950
1951  ACTGGGGTTCCGGGCAGCCGTGGGTCATCACGGAGCTGATGGGAGCGACACTGCGATAGGAGATG   2015
2016  TAGCCGAACCAGCCCCCAGGTCCCCGACCCCGGTACGCGACCCCTGGACAGCTGAGTGCGGCCCA   2080
2081  GCCTGCACCGCCTCAGACCTGGGGTGAGCCAGCTATGCCCAGCGGTGCCTCGTCTCCAGGTCCTG   2145
2146  GAGCTGGGAGAGTCATGGGTCCCGACTGTGTCCCACCCTCCTCCGTGTCTCCAGAGTCACCGGC   2210
2211  CAGAACTGCCCCCAGTGTCCCGACCTGCTCAGGGTCGTGTCCAGCCCC                   2258
```

*ZeroBlunt Vector from Invitrogen

SEQUENCE LISTING

```
<160> NUMBER OF SEQ ID NOS: 12

<210> SEQ ID NO 1
<211> LENGTH: 587
<212> TYPE: DNA
<213> ORGANISM: Bovine

<400> SEQUENCE: 1
agctcgagat gaacccactg tggaccctcc tctttgtgct ctcagccccc agagggtcc      60 tgtcccaggt gcagctgcgg gagtcgggcc ccagcctggt gaagccgtca cagaccctct    120
cgctcacctg cacggcctct ggattctcat tgagcgacaa ggctgtaggc tgggtccgcc    180
aggctccagg gaaggcgctg gagtggctcg gtggtataga cactggtgga agcacaggct    240
ataacccagg cctgaaatcc cggctcagca tcaccaagga caactccaag agccaagtct    300
ctctgtcagt gagcagcgtg acaactgagg actcggccac atactactgt actactgtgc    360
accccagtcc tgatggttat agttatggtt atggttgtgg ttatggttat ggttgtagtg    420
gttatgattg ttatggttat ggtggttatg gttatggtgg ttatggtggt tatagtagtt    480
atagttatag ttatagtcca ggaaatacta cgtcgatgcc tggggccaag gactcctggt    540
caccgtctcc tcagaaggta atcacacccg agagtcttca ctagtct                  587

<210> SEQ ID NO 2
<211> LENGTH: 205
<212> TYPE: DNA
<213> ORGANISM: Bovine

<400> SEQUENCE: 2
```

```
gggtttctga tgccggctgt gtcacggtgg tagttgtcct gatggttata gttatggtta        60
tggttgtggt tatggttatg gttgtagtgg ttatgattgt tatggttatg gtggttatgg       120
tggttatggt ggttatggtt atagtagtta tagtttatagt tatacttacg aatataccac      180
agtgatactc tctgggacaa aaacc                                             205

<210> SEQ ID NO 3
<211> LENGTH: 115
<212> TYPE: DNA
<213> ORGANISM: Bovine

<400> SEQUENCE: 3
gggtttctga tgccggctgt gtcacggtgg tagttgttat agtggttatg gttatggttg        60
tggttatggt tatggttatg attataccac agtgacactc tctgggacaa aaacc            115

<210> SEQ ID NO 4
<211> LENGTH: 99
<212> TYPE: DNA
<213> ORGANISM: Bovine

<400> SEQUENCE: 4
gggtttctga tgccggctgt gttgtggtga tgatacgata ggtgtggttg tagttattgt        60
agtgttgcta ccacagtgat gctctcagtg tcagaaacc                               99

<210> SEQ ID NO 5
<211> LENGTH: 139
<212> TYPE: DNA
<213> ORGANISM: Bovine

<400> SEQUENCE: 5
ccccagtcct gatggttata gttatggtta tggttgtggt tatggttatg gttgtagtgg        60
ttatgattgt tatggttatg gtggttatgg ttatggtggt tatggtggtt atagtagtta      120 tagtttatagt tatagtcca                                                   139

<210> SEQ ID NO 6
<211> LENGTH: 2258
<212> TYPE: DNA
<213> ORGANISM: Bovine

<400> SEQUENCE: 6
gcgtggccac ccaccacccc acaggtcagc ctggggagct caagacggac tggcgtccct        60
acctgccagg ttcctgtgca ggatgctgtc cacggccgca atgctttggc ctctgctcag       120
cttctgaggt tctccggccc accaccactg acctgaatgg gcttggagtg caggcccagc       180
tgaacatcag acctgggctc agagagccac tcggtccagg gtgcactcag ccgtgcacct       240
ggaggagggt cctccatgcc gcagggttgg ctgggcaagg aggcatcaca gaccaccctg       300
ctgttgggac gtccagccct ggaccaggac taggttctca gaatcctccc caccacggga       360
cctgtccata cctggaccag ctgacagctc ccaagggctc caacccagca gacaagacca       420
agggcgctga aggcgagcag ctagggtttc tgatgccggc tgtgttgtgg tgatgatacg       480
ataggtgtgg ttgtagttat tgtagtgttg ctaccacagt gatgctctca gtgtcagaaa       540
cccctgcccc gaggtcccag accagggagc ctgtcctcca ggtacgggc accgccctgc       600 cctcgtgacc atcagactgc accctgcacg cctcaccct gctgtctcag gcagcaaca        660 gcctctggag gagtcctggg ccaggcactc ggctgtggag tcccagacaa tgatagcctc       720
```

```
                                       -continued agcagtttcc agccacctga ccctggagga gcttgtgcaa gctggaggcc ggctggggcc      780
cggagcctca gaaccctccc tgccagggg cccgtccaga cctggaccag ctgacagctc      840
ccgaggactg cacgcccacc agacgagacc aaggggcgc tgaaggccag cagctggggt      900
ttctgatgcc ggctgtgtca cggtggtagt tgtcctgatg gttatagtta tggttatggt      960
tgtggttatg gttatggttg tagtggttat gattgttatg gttatggtgg ttatggtggt     1020
tatggtggtt atggttatag tagttatagt tatagttata cttacgaata taccacagtg     1080
atactctctg gacaaaaac ccctgccct gagggtccac ggccagggat cctggaggct      1140
gtgtttgggg cacgccctgc cctcctgcca ttggactaca acctgcacgc cctcaccctg     1200
ctgactcggg cagcaacagc ttaagataag agtcctgggc caggcgctgg gctgtggata     1260
cccagacaat gagatctcca gcaggttccc acctcctgac cctggaggaa cttccgcagc     1320
cctgtggcag gctggggacc gaccctaaga accctccccc cgcagggccc gtccagacct     1380
gaaccagctg acagctcccg agggctccac gcccccaga cgagaccaag ggggcgccga     1440
aggccagcag ctggggtttc gatgccggct gtgtcacggt ggtagttgtt atagtggtta     1500
tggttatggt tgtggttatg gttatggtta tgattatacc acagtgacac tctctgggac     1560
aaaaacccct gccctgagg gtccacggcc aggatcctg taggctgtgt ttggggcacc      1620
gccctgccct cctgaccatc ggactgcacc ctgcacgccc tcaccgggct gtctcagggc     1680
agcaagagcc tcaggaagga gtcgctgggc caggagctgg gctgcggaga cccagacagg     1740
agaccctcag cagctcccgc ccctgactct gcaggaactt gtgcaggcct gaggcaggct     1800
gggcttctgc tgggacgcca tggtctcagc cacccatatc gacggccaca ggcgggcagt     1860
gggccaggat cagactcaaa ggcccacact tccgggtcct gtcctgcccg gcagcccaac     1920
ctggtcacag aggtcccagg cctgtggccc actggggttc cgggcagccg tgggtcatca     1980
cggagctgat gggagcgaca ctgcgatagg agatgtagcc gaaccagccc ccaggtcccc     2040
gaccccggta cgcgaccct ggacagctga gtgcggccca gcctgcaccg cctcagacct      2100
ggggtgagcc agctatgccc agcggtgcct cgtctccagg tcctggagct gggagagtca     2160
tgggtcccga ctgtgtcccc accctcctcc gtgtctccag agtcaccggc cagaactgcc     2220
cccagtgtcc cgagctgctc agggtcgtgt ccagccccc                             2258

<210> SEQ ID NO 7
<211> LENGTH: 19
<212> TYPE: PRT
<213> ORGANISM: Artificial Sequence
<220> FEATURE:
<223> OTHER INFORMATION: Human HIV-1

<400> SEQUENCE: 7

Arg Lys Ser Ile His Ile Gly Pro Gly Arg Ala Phe Tyr Thr Thr Gly
1               5                   10                  15

Glu Ile Ile

<210> SEQ ID NO 8
<211> LENGTH: 19
<212> TYPE: PRT
<213> ORGANISM: Artificial Sequence
<220> FEATURE:
<223> OTHER INFORMATION: Viral - Foot and Mouth Disease VP1 Protein

<400> SEQUENCE: 8

Met Asn Ser Ala Pro Asn Leu Arg Gly Asp Leu Gln Lys Val Ala Arg
1               5                   10                  15
```

```
Thr Leu Pro

<210> SEQ ID NO 9
<211> LENGTH: 11
<212> TYPE: PRT
<213> ORGANISM: Artificial Sequence
<220> FEATURE:
<223> OTHER INFORMATION: Viral - Influenza A

<400> SEQUENCE: 9

Ser Phe Glu Arg Phe Glu Ile Phe Pro Lys Glu
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Viral - PR8 Influenza

<400> SEQUENCE: 10

Thr Thr Gly Arg Thr Arg Ala Leu Val Arg Thr Gly Met Asp Pro
1               5                   10                  15

<210> SEQ ID NO 11
<211> LENGTH: 22
<212> TYPE: DNA
<213> ORGANISM: Artificial Sequence
<220> FEATURE:
<223> OTHER INFORMATION: left hand primer

<400> SEQUENCE: 11
agctcgagat gaacccactg tg                                              22

<210> SEQ ID NO 12
<211> LENGTH: 24
<212> TYPE: DNA
<213> ORGANISM: Artificial Sequence
<220> FEATURE:
<223> OTHER INFORMATION: right hand primer

<400> SEQUENCE: 12
agactagtga agactctcgg gtgt                                            24
```

BOVINE GERMLINE D-GENES AND THEIR APPLICATION

This application is a continuation-in-part of U.S. patent application Ser. No. 10/125,594 filed Apr. 19, 2002 U.S. Pat. No. 6,740,747 which claims the benefit under 35 USC §119(e) from U.S. Provisional patent application Ser. No. 60/284,899, filed Apr. 20, 2001.

FIELD OF THE INVENTION

The present invention relates to novel bovine germline D-genes that, also, provide D-gene specific DNA probe. The unique composition of bovine germline D-genes permits testing and analysis of germline D-gene composition of breeding cattle stock for sustaining optimum capacity for antibody diversification. The sustenance of maximum D-gene pool in breeding cattle stock is essential for enhanced immunocompetence and species survival. The availability of bovine germline D gene sequence(s) and specific DNA probe provide molecular genetic marker for use in selective breeding strategies of breeding cattle stock. The novel D-genes are unique to cattle and, therefore, are useful for forensic analysis of tissue suspected of cattle origin.

BACKGROUND OF THE INVENTION

One of the most remarkable characteristics of the immune system is its ability to generate a large and diverse repertoire of antibody molecules that specifically recognize the native form of epitope(s) of potential pathological consequence in an attempt to protect the organism. Such a diversity that protects an organism from a variety of infectious pathogens and toxic substances has been exploited to produce high affinity receptors/antibody for use in immunodiagnostics, molecular probes and immunotherapy. For some applications, it is necessary to reduce antibody size to improve biodistribution, and reduce immunogenicity and side reactions arising from antibody effector functions. The Fv, consisting of associated $V_H$ and $V_L$ domains, constitutes the minimum functional antigen-binding fragment of a conventional antibody. Because of the inherent instability of $V_H$-$V_L$ Fv heterodimers, single domain antibody, i.e., $V_H$ only, is expected to be stable because of its small size. This may be particularly so as homodimers of heavy (H)-chain alone occur naturally as antibody in camels. The murine $V_H$s, unlike camel, are 'sticky' because of exposure of a large hydrophobic surface spanning 500–800 $A^o$. In addition to poor solubility behaviour the murine $V_H$s have an average CDR3H length of 9 amino acids in contrast to human (12 residues) and camels (14 residues). Thus, the potential antigen-binding surface of murine $V_H$ is smaller as compared to human antibodies of potential therapeutic significance. A Fv or single domain antibody with a longer CDR3H is, therefore, of potential interest from an antibody engineering perspective as it would potentially provide large antigen surface binding area.

The variable-region of immunoglobulin (Ig) bear V-region epitope capable of stimulating both humoral and cellular immune responses upon hetero-, allo or iso-immunization (Nisonoff, A. and Lamoyi, E. 1981. Implication of the presence of an internal image of the antigen in anti-idiotypic antibodies: possible application to vaccine production. Clin. Imm. Immunopath. 21:397–406; Zaghouani, H. et al. 1993. Presentation of a viral T cell epitope expressed in the CDR3 region of a self-immunoglobulin molecule. Science 259: 224–227; Zaghouani, H. et al. 1993. Engineered immunoglobulin molecules as vehicles for T cell epitope. Intern. Rev. Immunol. 10:265–278). The V-region epitope of an Ig often correlates with the amino acid composition of the CDR regions. Since the CDR loops vary both in composition and size, these provide permissive sites for foreign (e.g., microbial origin) epitope insertion that would create an antigenized Ig of desired epitope. Prior research indeed demonstrates the ability to manipulate the entire CDRS of an immunoglobulin for generation of functional chimeric antibodies of interest (Morisson, Science 229:1202; Jones et al.1986. Nature 321:522; Verhoeyen et al. 1988. Science. 239:1534; Riechmann et al. 1988. Nature 332:323). Antigenization of immunoglobulin is, however, hindered by shorter CDRs in immunoglobulins from mice and man that permit incorporation of T cell epitopes (linear) but not B cell epitopes (conformational) for use as vaccine vectors.

The inventors observed that approximately 9% of VDJ rearrangements encode functional bovine IgM antibody with a CDR3H length up to 61 amino acids with multiple cysteine residues (Saini, 1999). Such an exceptionally long CDR3H is generated by unusually long germline D-genes with unique composition that exist in cattle (Farbod Shojaei, MSc Thesis (2001). Molecular aspects of bovine DH genes. University of Guelph, Guelph) and is the first ever to be documented in a species and is of significant interest to exploit its potential in engineering antibodies, either as Fv or single domain, of diagnostic and therapeutic significance. In addition to the long CDR3H, the configurational diversity from such a long primary sequence with multiple even numbered cysteine residues is expected to contribute to the immunoglobulin fold capable of binding to an infinite array of chemical structures. In addition, bovine germline D genes provide molecular genetic marker for cattle breeding strategies and forensic analysis.

SUMMARY OF THE INVENTION

Antigenization of immunoglobulin is hindered by shorter CDRs in immunoglobulins from mice and man that permit incorporation of T cell epitopes (linear) but not B cell epitopes (conformational) for use as vaccine vectors. The bovine VDJ cassette developed by the inventors provides the novel ability of the immunoglobulin molecule to incorporate both linear T cell epitopes (CDR1H and CDR2H) as well as conformational B cell epitopes (CDR3H). As a result, the germline encoded BF1H1 VDJ cassette isolated by the inventors from bovine fetal B cells is suitable for immunoglobulin antigenization with both B and T cell epitopes and use as vaccine vector. In addition, multiple epitopes can be incorporated and, thus, provide opportunity for development of multivalent vaccine. The isolation of expressed recombined VDJ genes capable of encoding CDR3H length >50 amino acids are the first ever to be documented in any species. The VDJ cassette isolated from cattle provides a natural source of immunoglobulin that is capable of incorporating multiple, both T and B cell epitopes, and is, therefore, most suitable as a vaccine vector across species by using species specific different isotypes, as or if required. The antigenized immunoglobulin incorporating both T and B cells of interest would be especially useful for development of oral vaccines for use in humans.

The long CDR3H in BF1H1 VDJ rearrangement originates from long germline D-genes so far known to exist in cattle only. The bovine germline D-genes provide novel approach for sustaining maximum capacity for antibody diversification in cattle essential for immunocompetence via selective breeding strategies that incorporate testing for D genes as molecular biomarker. The novel gene elements, such as D-genes, are unique to cattle and, therefore, are of considerable use in forensic analysis as well. The isolation and sequencing of the D-genes allows the preparation of D-gene specific probes that can be used to unambiguously identify bovine tissue.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. BFH1 Cassette

Figure 1:
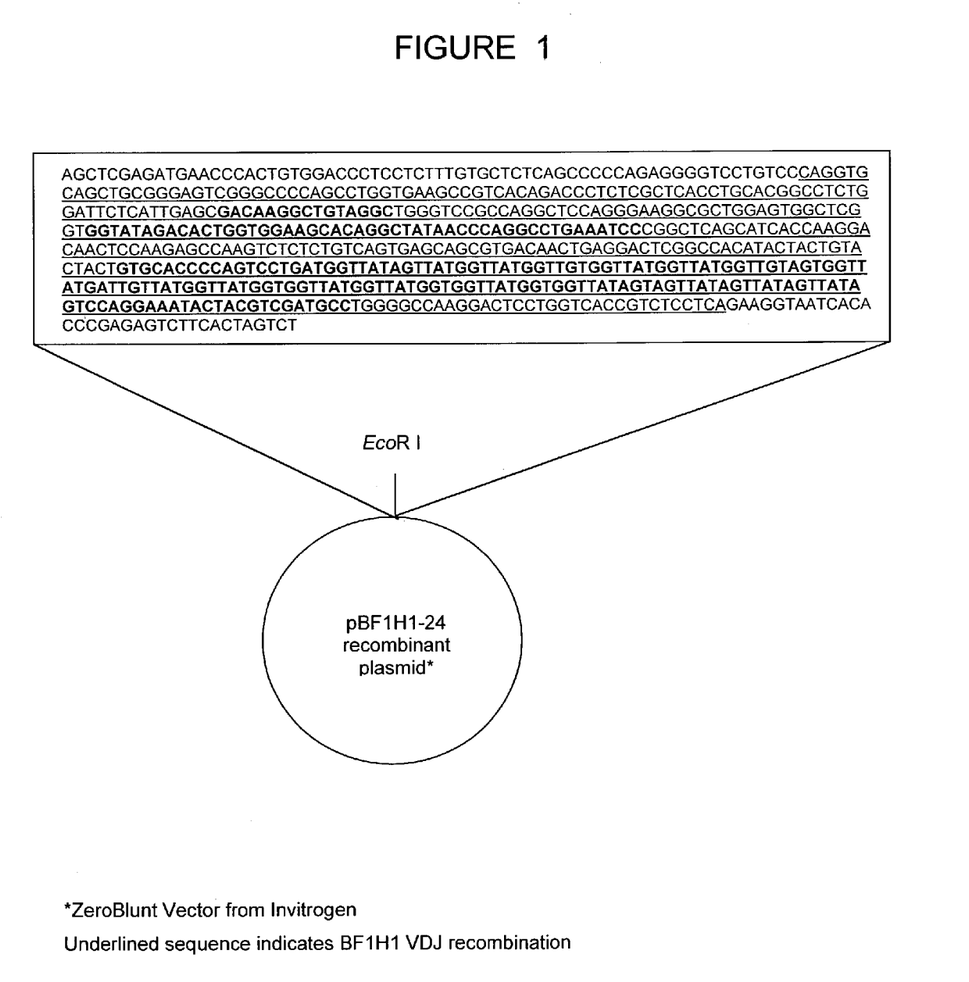
FIG. 1(SEQ ID NO:1) shows the BF1H1 VDJ recombination sequence and recombinant pBF1H1-24 plasmid map. The CDR1, CDR2 and CDR3 are shown in bold and the complete VDJ sequence is underlined. Note the exceptionally long CDR3H region that is suitable for insertion of conformational single or multiple epitope(s).

The present invention described here provides a novel variable-region (V-D-J) gene recombination, termed BF1H1 expressed naturally in cattle. FIG. 1 shows the nucleic acid sequence of BF1H1 (SEQ ID NO:1) and the plasmid map of the recombinant BF1H1-24. Accordingly, in one embodiment the present invention provides an isolated bovine VDJ gene comprising the nucleic acid sequence shown in FIG. 1 (SEQ ID NO:1). In another embodiment, the present invention provides a recombinant plasmid comprising the nucleic acid sequence of SEQ ID NO:1, preferably the plasmid is pBF1H1-24 as shown in FIG. 1.

Figure 2:
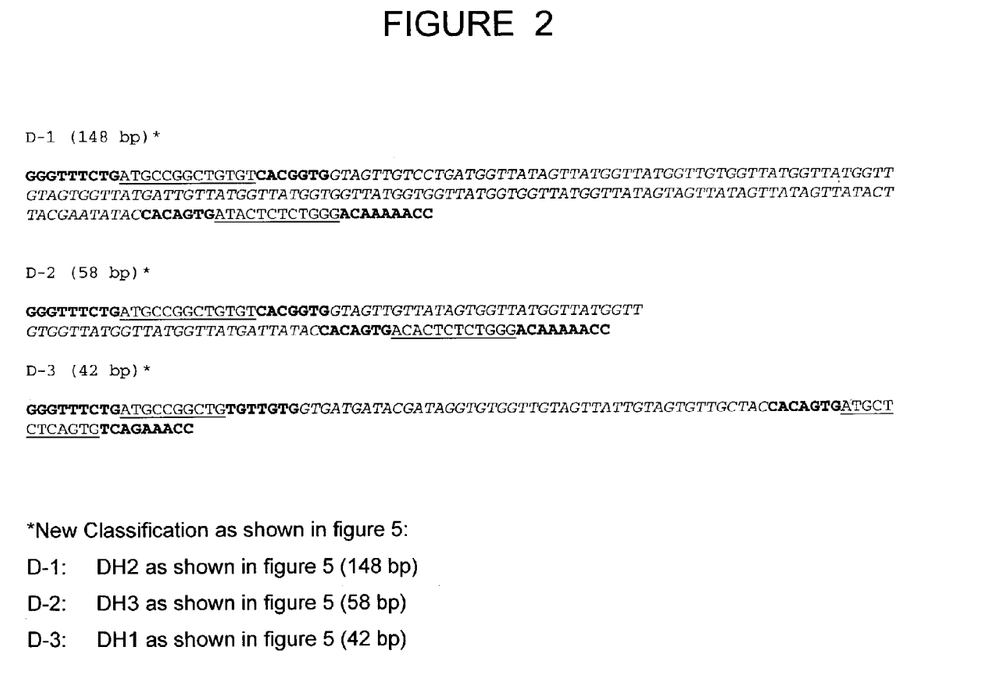
FIG. 2 (SEQ ID NOS:2–4) shows the bovine germline D-gene sequences obtained from pBGD14S recombinant plasmid derived from 2–11C lambda phage isolated from bovine genomic library (Stratagene, USA). Note that the recombination signal sequences (RSS) are shown in bold and the spacers are underlined. The D-genes are shown in italic. The novel D-gene sequence has been isolated from bovine genome that provides the structural basis for generation of an exceptionally long CDR3H.
Figure 3:
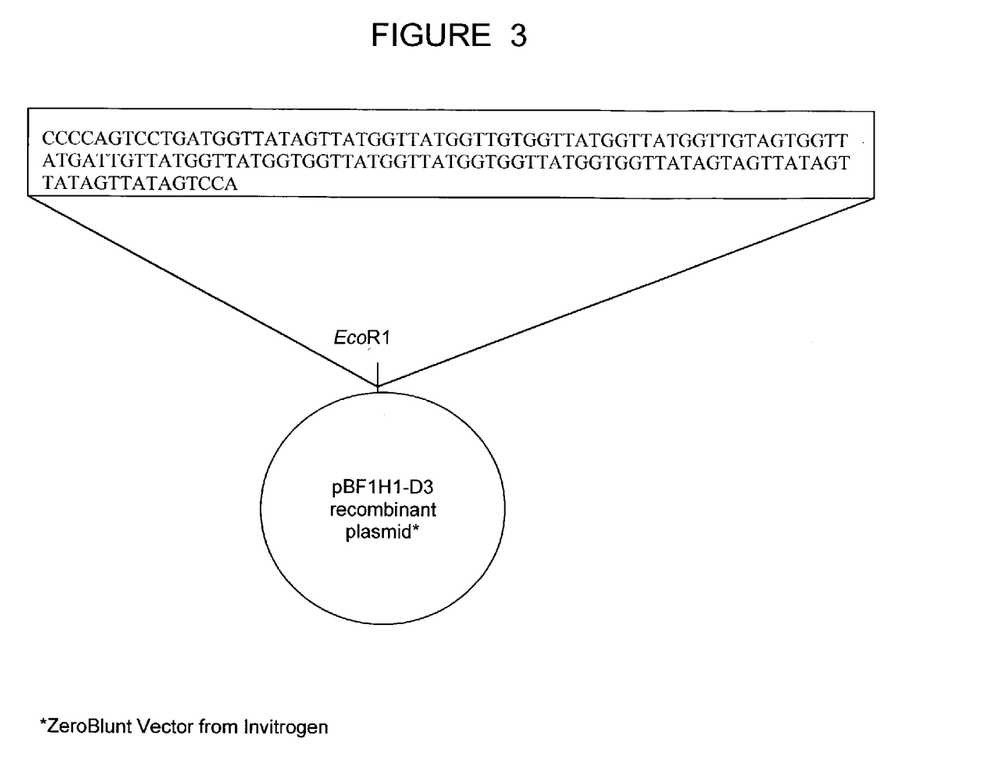
FIG. 3 is the map of recombinant plasmid pBF1H1-D3 and the cloned nucleotide sequence (SEQ ID NO:5) corresponding to D-gene encoded region of the CDR3H of BF1H1 VDJ rearrangement. The pBF1H1-D3 plasmid upon digestion with EcoR1 restriction enzyme provides approximately 139 base pair DNA fragment suitable to probe D-genes by methods such as restriction fragment length polymorphism (RFLP).
Figure 5:
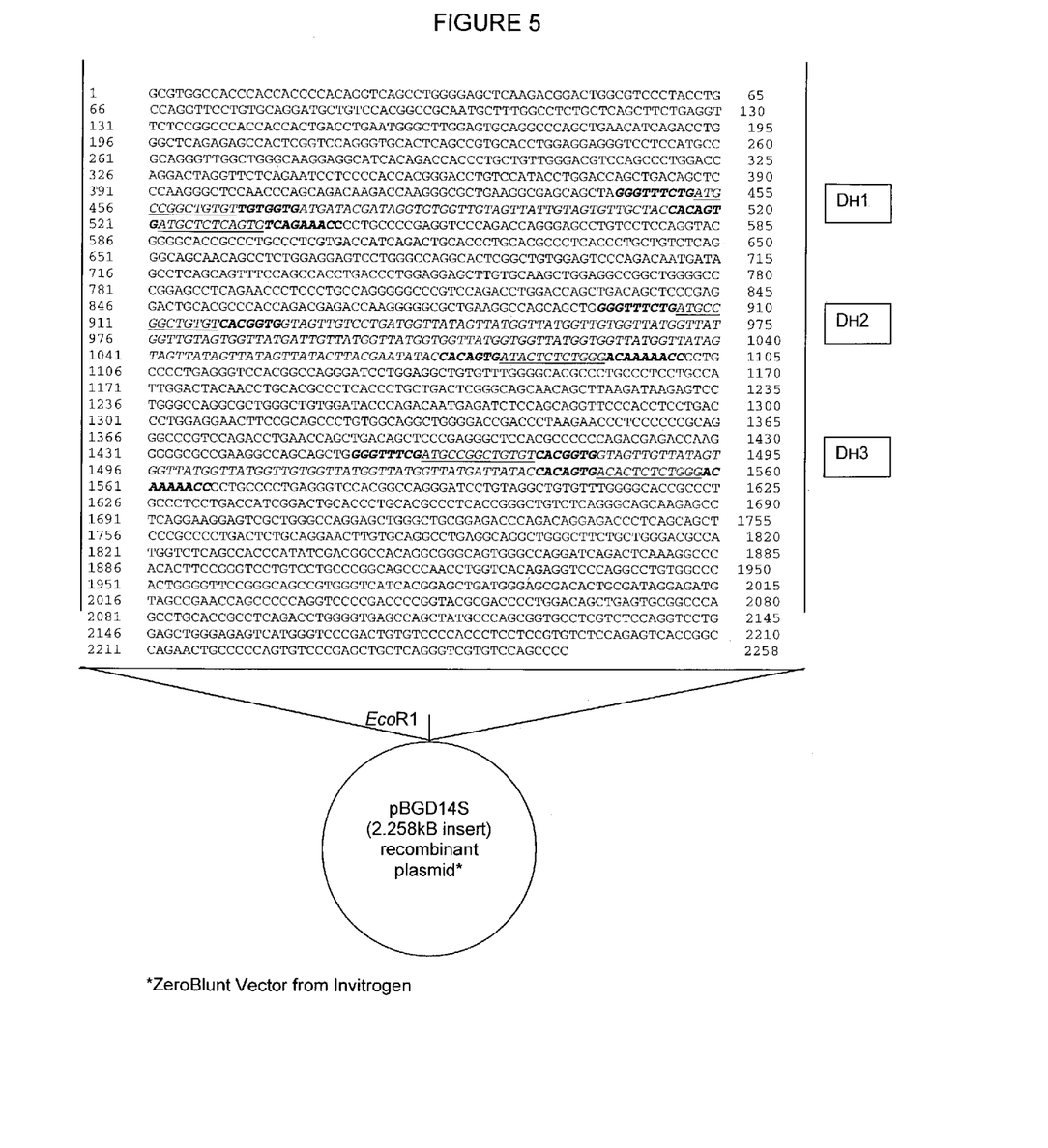
FIG. 5 (SEQ ID NO:6) shows the germline D-gene sequence, incorporating DH1, DH2 and DH3 genes together with recombination signal sequence (RSS) including the intervening introns in recombinant plasmid, pBGD14S (2.258 kB insert). The RSS are shown in bold and underlined both on the 5' and 3' end of each D-gene.

The long CDR3H in the BF1H1 VDJ rearrangement comes from the unusually long germline D-genes. The novel long D-gene segments that encode most of the CDR3H region are shown in FIGS. 2 (SEQ ID NOS:2–4). Accordingly, in a further embodiment, the present invention provides an isolated bovine germline D-gene comprising the nucleic acid sequence of D-1 (SEQ ID NO:2), D-2 (SEQ ID NO:3) and/or D-3 (SEQ ID NO:4) as shown in FIG. 2. In another embodiment, the present invention provides an isolated 2.258 kB bovine genomic germline D-gene sequence, incorporating DH1, DH2 and DH3 genes together with the intervening introns, comprising the nucleic acid sequence as shown in FIG. 5 (SEQ ID NO:6). In yet another embodiment, the present invention provides a recombinant plasmid comprising the nucleic acid sequence of SEQ ID NO:6, preferably the plasmid is pBGD14S shown in FIG. 5 or pBF1H1-D3 shown in FIG. 3.

In all embodiments of the invention, the term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The invention also extends to modifications that one of skill in the art can make to the nucleic acid sequences of the invention. Accordingly, the present invention provides:

(a) a nucleic acid sequence as shown in SEQ ID NO:1, SEQ ID NO:2, SEQ ID NO:3, SEQ ID NO:4, SEQ ID NO:5 or SEQ ID NO:6 wherein T can also be U;

(b) a nucleic acid sequence that is complimentary to a nucleic acid sequence of (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner. The variations may be attributable to local mutations or structural modifications. Nucleic acid sequences having substantial homology include nucleic acid sequences having at least 65%, more preferably at least 85%, and most preferably 90–95% identity with the nucleic acid sequences as shown in SEQ ID NO:1, SEQ ID NO:2, SEQ ID NO:3, SEQ ID NO:4, SEQ ID NO:5 or SEQ ID NO:6.

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1–6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in SEQ ID NO:1, SEQ ID NO:2, SEQ ID NO:3, SEQ ID NO:4, SEQ ID NO:5 or SEQ ID NO:6 with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID NO:1, SEQ ID NO:2, SEQ ID NO:3, SEQ ID NO:4, SEQ ID NO:5 or SEQ ID NO:6. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The invention includes the exceptionally long CDR3H region together with CDR1 and CDR2 suitable for preparation of novel immunoglobulin entities, such as antigenized immunoglobulin (T and B cell epitope insertion) for immunization and engineered antibodies for therapy and diagnosis, using recombinant antibody technology. In addition, DNA probe to D-gene (pBF1H1-D3) or use of novel D-gene sequence for use in animal selection strategies for antibody gene sustenance for disease resistance for use in techniques involving RFLP (restriction length polymorphism) or PCR assays or DNA sequencing or similar novel technologies that may arise in future.

II. Uses

The present invention includes all uses of the novel nucleic acid sequences and plasmids of the invention, including (but not limited to) some of the uses described below.

(a) Genetic Engineering and Antigenization of Immunoglobulin with T and B Cell Epitopes.

In one application, the BF1H1 VDJ gene sequence (SEQ ID NO:1) and the recombinant plasmid pBF1H1-24 (FIG. 1) is suitable for antigenization. The CDR1, CDR2 and CDR3 (shown in bold in FIG. 1) provide the sites for CDR grafting and antigenization of both T and B cell epitopes. Multiple epitope(s) can be grafted in these sites.

The term "B cell epitope", often conformational in nature, refers to an amino acid sequence part of an antigen recognized and/or capable of binding to an immunoglobulin receptor of a B cell involved in induction of antibody secretion by a B lymphocyte.

The term "T cell epitope", often linear in nature, refers to a peptide sequence originating from an antigen that associates with MHC molecules and recognized by a T cell leading to its being triggered into an effector T cell demonstrable by its activation, e.g., proliferation assay, and secretion of cytokines. This includes epitopes recognized by both T helper ($T_H$) and T cytotoxic ($T_C$) lymphocytes. According to the present invention, the BF1H1 cassette is capable of sustaining relatively long conformational B cell epitope in their CDR3H region because of sustaining folding ability of its framework region of a large sized CDR3H (>50 amino acids). The T cell epitopes can be inserted into CDR1 and CDR2 as well, though their possible insertion in the CDR3H is not excluded. A chimeric molecule carrying an inserted epitope can be generated by methods analogous to those described by Zaghouani et al. 1993, Science. 259:224–227 together with standard recombinant techniques (Sambrook et al. 1989. Molecular Cloning—A laboratory Manual, $2^{nd}$ edition, Cold Spring Harbor Laboratory, USA) and PCR mutagenesis (Zaghouni et al. 1992. J. Immunol. 148:3604).

The methods for identifying B cell epitopes have been described (Caton et al. 1982. Cell. 31:417–27). For example, and not by way of limitation, the V3 loop of the envelope protein of human immunodeficiency virus (HIV) type 1 is known to be a B cell epitope. Despite variation in the sequence of this B cell epitope, following consensus sequence corresponding to amino acids 301 to 319 of gp120 protein of HIV-1 is defined: R-K-S-I-H-I-G-P-G-R-A-F-Y-T-T-G-E-I-I (SEQ ID NO:7).

This epitope comprises 19 codons and CDR3H region of the BF1H1 VDJ cassette provides a suitable site for insertion where it would be exposed into the solvent. The BF1H1 VDJ cassette is capable of sustaining even longer B cell epitopes and/or multiple B cell epitopes that would be exposed via CDR3H loop. Many examples of defined B cell epitope(s) are known to exist. As for animal viral diseases, a B cell epitope of Foot and Mouth Disease VP1 protein, amino acids 141–160, is identified (Clarke et al. 1987. Nature. 330:381–84) as shown: M-N-S-A-P-N-L-R-G-D-L-Q-K-V-A-R-T-L-P (SEQ ID NO:8).

The methods for identifying T cell epitopes, both T helper and T cytotoxic, have been described (Rotzschke et al. 1991. *Immunology Today* 12:447–455). For example, and not by way of limitation, T helper epitope on influenza A hemagglutinin (HA) protein corresponds to amino acids at position 110–120 as shown: S-F-E-R-F-E-I-F-P-K-E (SEQ ID NO:9).

This epitope comprises 11 codons and CDR2 and CDR3H region of the BF1H1 VDJ cassette provide a suitable site for insertion where it would be exposed into the solvent. Again, multiple T cell epitopes can be inserted in the CDR3H due to the ability to sustain longer CDR3 loop size. Another example of T cytotoxic epitope would be the residues 147–161 that correspond to PR8 influenza virus nucleoprotein as shown: T-T-G-R-T-R-A-L-V-R-T-G-M-D-P (SEQ ID NO:10).

The available methods are likely to define various T cell epitopes in the future.

Once the antigenization of immunglobulin is achieved (Zaghouani et al. 1993, Science. 259:224–227; Sambrook et al. 1989. Molecular Cloning—A laboratory Manual, $2^{nd}$ edition, Cold Spring Harbor Laboratory, USA; Zaghouni et al. 1992. J. Immunol. 148:3604; Innis, M. A., Gelfand, D. H. and Sninsky, J. J. 1995. PCR Strategies. Academic Press, New York), its functionality is confirmed by transfection technology. The chimeric immunoglobulin is cloned in an appropriate expression vector including, but not limited to plasmids and viruses, and their choice will depend upon the host used for protein expression. Suitable hosts include and are not limited to bacteria, insect cells, mammalian cells, and transgenic animals including rodents. The methods for gene transfer include the known methods including transfection, viral infection, retroviral latent infection, electroporation, liposome-mediated transfer, microinjection etc. Any suitable method for purifying proteins already known to exist may be used (Webb et al. 1989. PNAS, USA. 85:7731–7735; Moran et al. 1987. Viral Immunol. 1:1–12).

Further modifications of the VDJ cassette for developing specific high affinity receptors/antibody for use in immunodiagnostics, molecular probes and immunotherapy is also another possibility. For some applications, it is necessary to reduce antibody size to improve biodistribution, and reduce immunogenicity and side reactions arising from antibody effector functions. The Fv, consisting of associated $V_H$ and $V_L$ domains, constitutes the minimum functional antigen-binding fragment of a conventional antibody. Because of the inherent instability Of $V_H$–$V_L$ Fv heterodimers, single domain antibody, i.e., $V_H$ only, is expected to be stable because of its small size. A Fv or single domain antibody with a longer CDR3H is, therefore, of potential interest from an antibody engineering perspective as it would potentially provide large antigen surface binding area. General antibody engineering methods are known and have been in practice (Borrebaeck, C.A.K. 1995. Antibody engineering. $2^{nd}$ edition. Oxford University Press. New York).

(b) Detection and Selection for Antibody Gene Pool Sustenance for Animal Breeding Strategies and Forensic Purposes.

In another application, the germline D-gene(s) sequence (D-1 (SEQ ID NO:2), D-2 (SEQ ID NO:3) and D-3 (SEQ ID NO:4); FIG. 2) contained in the cloned 2.258 kB plasmid pBGD14S (FIG. 5) and, also plasmid pBF1H1-D3 (FIG. 3) containing 138 base pair sequence specific to bovine D-genes (SEQ ID NO:5) (source of DNA probe specific for bovine germline D-genes), that are unique to cattle for use as genetic molecular marker in cattle breeding strategies for gene pool sustenance and forensic analysis. The bold and underlined sequence represents the recombination signal sequences (RSS) and the sequence in between represents the germline D-gene (FIG. 5, SEQ ID NO:6).

Accordingly, the present invention includes the preparation and use of nucleic acid probes based on the novel sequences of the germline D-genes and recombined VDJ genes described herein. The probes can include fragments of the nucleic acid sequences shown in SEQ ID NOS:1 to 6 and will be capable of hybridizing with the complement of a nucleic acid sequence shown in SEQ ID NOS:1 to 6.

Accordingly, the present invention provides a method for detecting a bovine germline D-gene in a sample comprising contacting the sample with a nucleotide probe capable of hybridizing with the complement of nucleic acid molecule shown in SEQ ID NOS:2, 3, 4, 5 or 6 to form a hybridization product, under conditions which permit the formation of the hybridization product, and assaying for the hybridization product.

The present invention also provides a method for detecting a VDJ gene in a sample comprising contacting the sample with a nucleotide probe capable of hybridizing with the complement of nucleic acid molecule shown in SEQ ID NO:1 to form a hybridization product, under conditions which permit the formation of the hybridization product, and assaying for the hybridization product.

The nucleotide probes used in the above assays may be labelled with a detectable substance such as a radioactive label which provides for an adequate signal and has sufficient half-life such as 32P, 3H, or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes that hybridize to the nucleic acid molecule of the present invention preferably, nucleic acid molecules which hybridize to the nucleic acid molecule of the invention under stringent hybridization conditions as described herein.

In one embodiment, the hybridization assay can be a Southern analysis where the sample is tested for a DNA sequence that hybridizes with a D-gene or VDJ gene specific probe. In another embodiment, the hybridization assay can be a Northern analysis where the sample is tested for an RNA sequence that hybridizes with a D-gene or VDJ gene specific probe. Southern and Northern analyses may be performed using techniques known in the art (see for example, Current Protocols in Molecular Biology, Ausubel, F. et al., eds., John Wiley & Sons).

Nucleic acid molecules to be detected can be selectively amplified in a sample using the polymerase chain reaction (PCR) methods and cDNA or genomic DNA. It is possible to design synthetic oligonucleotide primers from the nucleic acid sequences shown in SEQ ID NOS:1 to 6 for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

Samples may be screened routinely using probes to detect the presence of bovine D-genes or VDJ recombinations by a variety of techniques. Genomic DNA may be obtained from bovine cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to D-gene or VDJ gene sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these sequences is then visualized using methods such as autoradiography, fluorometry, or calorimetric reaction. Suitable PCR primers can be generated which are useful for example in amplifying portions of the subject sequence.

PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as would be understood by those skilled in the art.

The recombinant plasmid, pBF1H1D3 (FIG. 3, SEQ ID NO:5), is also suitable for use as DNA probe to detect unique bovine D-genes for use as a molecular probe for antibody gene pool sustenance via selective cattle breeding and, also, for forensic analysis. The pBF1H1-24 recombinant plasmid also provides a source of DNA probe specific to bovine $V_H$ gene for their detection and analysis. Limited germline diversity exists for antibody genes in cattle (Saini, S. S., Hein, W. and Kaushik, A. 1997. A single polymorphic immunoglobulin $V_H$ gene family related to mammalian group I, clan II, is identified in cattle. Molecular Immunology. 34:641–651; Surinder Saini, PhD Thesis (1999). "Molecular immunogenetics of bovine antibody", University of Guelph, Guelph, Ontario, Canada) in contrast to other species such as man and mouse. Limited germline antibody gene pool is deleterious to cattle health due to lowered host defense ability and species survival. Therefore, it is essential to employ cattle breeding strategies that aim to sustain the decreasing antibody gene pool in cattle.

The composition of recombination signal sequences (RSS) and D (diversity)-gene is unique in cattle (FIG. 2 and FIG. 5). Since D-genes contribute most to antibody diversity by making CDR3H the most variable of the three CDRs, these provide an ideal genetic molecular marker for typing of the cattle breeding stock to select for those with maximum gene pool in the germline in addition to production related markers. This would permit sustenance of antibody gene pool for better cattle health and long term species survival under wild environmental conditions. The bovine D-genes (SEQ ID NO:6, FIG. 5) provides a useful molecular marker for breeding cattle selection by DNA typing with known techniques such as restriction fragment length polymorphism (RFLP) and DNA sequencing (Surinder Saini, PhD Thesis (1999). "Molecular immunogenetics of bovine antibody", University of Guelph, Guelph, Ontario, Canada) such as RFLP, also known as DNA fingerprinting). Another approach would be to develop PCR assays based on known methods (Innis, M. A., Gelfand, D. H. and Sninsky, J. J. 1995. PCR Strategies. Academic Press, New York) and the sequence composition (FIGS. 2 and 5) to type genomic DNA to determine the highest possible D-gene diversity in the germline of the breeding cattle stock.

The examples would include testing the genomic DNA from semen samples of the breeding bulls by RFLP, PCR assays and DNA sequencing for determining the number of D-genes in the breeding stock and to select those with maximum germline diversity at the D-gene loci in the breeding stock and to eliminate those with relatively reduced diversity in the germline.

Since the composition of recombination signal sequences (RSS) and D (diversity)-gene is unique in cattle (FIGS. 2 and 5), it provides a molecular tool to detect bovine DNA for forensic purposes in a variety of the samples by known recombinant DNA methods (Sambrook et al. 1989. Molecular Cloning—A laboratory Manual, $2^{nd}$ edition, Cold Spring Harbour Laboratory, USA) or PCR assays (Innis, M. A., Gelfand, D. H. and Sninsky, J. J. 1995. PCR Strategies. Academic Press, New York).

An example of forensic analysis may include testing the sample such as blood, soil etc. to detect bovine DNA that has unique D-gene sequence composition (SEQ ID NOS:2–6) to determine if it had contamination with bovine material. DNA sequencing would also help identify bovine DNA by comparison with the sequences outlined in FIG. 2 (SEQ ID NOS:2–3). Similarly, an adulteration from the bovine source may be detected for food safety purposes for animal and human health reasons by known methods (Sambrook et al. 1989. Molecular Cloning—A laboratory Manual, $2^{nd}$ edition, Cold Spring Harbor Laboratory, USA) or PCR assays (Innis, M. A., Gelfand, D. H. and Sninsky, J. J. 1995. PCR Strategies. Academic Press, New York).

The following non-limiting examples are illustrative of the present invention:

EXAMPLES

General and Specific Methods

1. Hybridoma: A mouse×bovine heterohybridoma (BF1H1), originating from splenic B cells of a 125-day-old bovine fetus via somatic fusion with X-63.Ag8.653 murine myeloma cells (Saini, S. S. PhD thesis, University of Guelph, 1999) was grown in RPMI 1640 (GIBCO BRL) supplemented with 10% horse serum, 5 mM sodium pyruvate, 5 mM MEM nonessential amino acids, 1 mM glutamin and 1% 100× antibiotic-antimycotic solution (GIBCO BRL, Canada).

2. Plasmid Preparation: The small-scale recombinant plasmids were isolated and purified using QIAprep Spin Miniprep Kit (QIAGEN, GmbH, Germany). The QIAGEN plasmid midi kit was used to extract plasmid DNA in large amount.

3. RNA Extraction: Approximately $10^7$ hybridomas were homogenized in 1 ml of Trizol reagent and RNA extracted as described earlier (Surinder Saini, PhD Thesis (1999). "Molecular immunogenetics of bovine antibody", University of Guelph, Guelph, Ontario, Canada; Saini, S. S., Allore, B., Jacobs, R. M. and Kaushik, A. 1999). Exceptionally long CDR3H region with multiple cysteine residues in functional bovine IgM antibodies. Eur. J. Immunol. 29:2420–26).

4. cDNA Synthesis and PCR: The cDNA was synthesized from total RNA using first strand cDNA synthesis kit (Pharmacia LKB, Uppsala, Sweden). The BF1H1 VDJ rearrangement was PCR amplified using left hand primer (5'AGCTCGAGATGAACCCACTGTG3' (SEQ ID NO:10)) corresponding to bovine $V_H$ gene leader sequence and right hand primer (5'AGACTAGTGMGACTCTCGGGTGT3' (SEQ ID NO:11)) corresponding to 5' sequence of bovine Cμ1 exon. The PCR conditions included a hot start at 94° C. for 2 minutes, denaturation at 96° C. for 1 minute, annealing at 60° C. for 30 seconds, and extension at 72° C. for 1 minute for a total of 30 cycles. The final extension step at 72° C. was performed for 10 minutes. An expected 571 bp fragment of VDJ rearrangement was gel fractionated at 1.5% agarose gel (Surinder Saini, PhD Thesis (1999). "Molecular immunogenetics of bovine antibody", University of Guelph, Guelph, Ontario, Canada; Saini, S. S., Allore, B., Jacobs, R. M. and Kaushik, A. 1999).

5. Bovine VH Gene Specific DNA Probe: The bovine $V_H$ gene specific DNA probe was prepared from a recombinant plasmid pb7S2 and radiolabeled as described (Surinder Saini, PhD Thesis (1999). "Molecular immunogenetics of bovine antibody", University of Guelph, Guelph, Ontario, Canada; Saini, S. S., Allore, B., Jacobs, R. M. and Kaushik, A. 1999).

6. Blunt Ending of PCR Amplified cDNA: The purified PCR product was blunt ended using T4 DNA polymerase (Pharmacia Biotech, Canada). Briefly, 38.25 μl of DNA was mixed with the appropriate buffer (50 mM Tris-Hcl pH 8.0, 5 mM MgcL, 5 mM DTT, 50 μg/ml BSA, 100:mol DNTPs) followed by the addition of 1 μl of T4 DNA enzyme. The mixture was incubated at 11° C. for 20 minutes and the reaction was stopped using 2 μl of 0.5 m EDTA.

Figure 4:
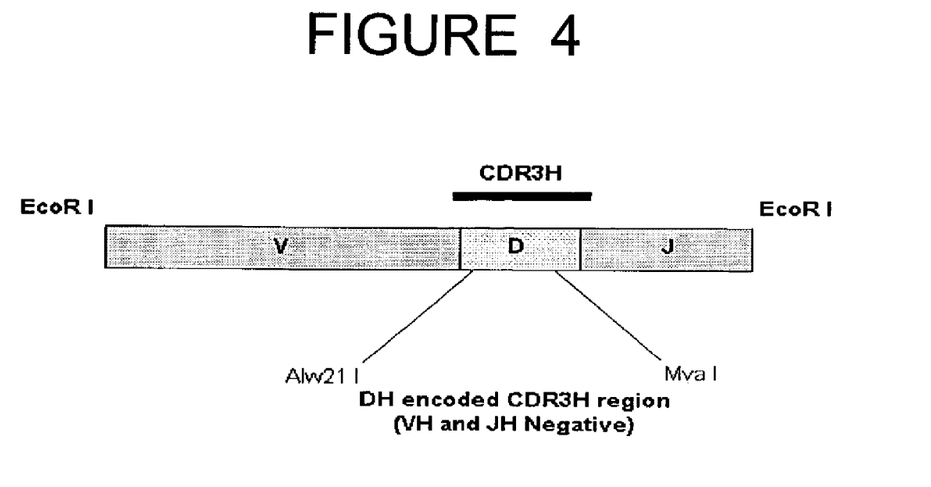
FIG. 4 is a schematic diagram of long CDR3H and restriction map for isolation of putative $D_H$ encoded CDR3H region of bovine antibody.

7. Development of DNA Probe to Putative Bovine DH Gene:

a. DNA Probe Design: The strategy to develop a DNA probe specific to DH encoded sequence is outlined in FIG. 4. The restriction map of BF1H1VDJ rearrangement shows that Alw21I and MvaI digestion results in $D_H$ encoded 139 bp fragment.

b. Cloning of BF1H1 VDJ Rearrangement: The blunt ended DNA was ligated in Zeroblunt vector (Invitrogen, USA) at 16° C. and used to transform Top 10 *E. coli* cells (Invitrogen, USA) by heat shock method. The transformed *E. coli* were grown on L.B medium containing Kanamycin (50 μg/ml) and colonies screened by EcoR1 restriction digestion, hybridization with recombinant pb7S2 DNA probe specific to $V_H$ encoded region. This led to isolation of recombinant plasmid, pBF1H1-24 (FIG. 1), that had successful cloning of BF1H1 VDJ rearrangement.

c. Cloning of $D_H$ Encoded CDR3H Region of Cloned BF1H1: The recombinant plasmid pBF1H1 24 was extracted followed by restriction digestion with EcoR1 to extract 571 bp VDJ fragment. The 571 bp fragment was further digested with Alw21I and MvaI and fractionated on a 6% PAGE to yield a 139 bp fragment that corresponded to $D_H$ encoded CDR3H region. The 139 bp DNA fragment was blunt ended by treating with T4 DNA polymerase (Phamacia Amersham Biotech, Canada), purified (QIAGEN, GmbH, Germany) and ligated into Zeroblunt vector (Invitrogen, USA). The ligated product was used to transform to Top 10 *E coli* (Invitrogen, USA). The recombinant plasmid isolated from two colonies was sequenced using M13 reverse and forward primers (MOBIX McMaster, CANADA). The pBF1H1-D5 (SEQ ID NO:5, FIG. 3) DNA fragment thus cloned was used as the DNA probe to detect putative bovine $D_H$ gene.

8. Screening of Bovine Genomic DNA Library to Isolate Bovine Germline $D_H$ gene: A bovine genomic DNA library (Startagene, USA) from the liver of 2-years old Holstein cow was plated out and its titer was determined to be $5.9 \times 10^{11}$ pfu/ml. The following steps were performed to isolate the bovine germline DH gene:

a. Host Strain Preparation: The XL-1 blue MRA P(2) strain (Stratagene, USA) was grown in LB medium with 0.2% maltose and 10 mM $MgSo_4$ at 30° C. overnight. The stock bacterial culture were prepared by growing bacteria to late log phase in 10 ml of L.B medium with 10 mM $MgSo_4$ and 2% maltose to which sterile glycerol liquid medium (50%) was added and 1 ml aliquots were stored at –70° C. The XL-1 Blue MRA P(2) strain (Stratagene, USA) was grown in LB medium (containing 2% maltose and 10 mM $MgSo_4$) at 30° C. for overnight and spun down at 2000 rpm at 4° C. for 10 minutes. The pellet were resuspended in 15 ml of 10 mM $MgSo_4$ to a dilution that corresponded to $OD_{600}=0.5$ with 10 mM MgSo4.

b. Lambda Phase Infection: Lambda phage diluted in SM buffer (0.58% Nacl, 0.2% $MgSo_4$, 0.05% Tris 1 molar pH 7.5, 0.5% of 2% Gelatin) at concentration of $1.5 \times 10^{-3}$ was added to 600 μL of XL-1 Blue MRA P2 ($OD_{600}=0.5$) cells (Stratagene, USA) followed by incubation at 37° C. for 15 minutes. Then, 4 ml of molten (48° C.) top agar (0.5% Nacl, 0.2% $MgSo_4$ 7H2O, 0.5% Yeast extract, 1% NZY amine, 1.5% agar, 0.7% agarose) was added on to the L.B plate agar. The plates were incubated overnight at 37° C. and number of plaques was counted to determine plaque forming unit/ml taking into consideration the dilution factor.

c. Screening of Bovine Genomic Library: The bovine lambda library (Stratagne, USA) was plated out at a titer of 700 pfu/ml/150 mm plate on NZY agar. The plates were incubated at 37° C. for overnight followed by chilling at 4° C. for 2 hours. The plaques were lifted on nitrocellulose (Boehringer Manheim, Germany) for 5 minutes and marked for orientation. The membrane was denatured in 1.5 M Nacl, 0.5 M NaOH for 3 minutes followed by neutralization in 1.5 M NaCl, 0.5 M Tris-Hcl (pH 8.0) for 5 minutes. The membrane was then rinsed in 0.2 M Tris-HCl (pH 7.5) and 2×SSC for 20 seconds. The DNA on the membrane was UV cross linked. The NZY agar plates containing lambda phage plaques were stored at 4° C. The membranes were prehybridized (50% formamide, 2× Pipes, 0.5% SDS and 10:g/ml heat denatured salmon Sperm DNA) at 42° C. for 6 hours. This was followed by hybridization with [$^{32}$-P]dCTP radiolabeled bovine DH gene specific (pBF1H1 D3) DNA probe at 42° C. for overnight. The membranes were then washed at high stringency and exposed to XAR-5 film for 24–72 hours at –70° C. This led to identification of a positive plaque, designated 2–11C lambda phage, which was lifted and placed into lambda dilution buffer (0.58% NaCl, 0.2%

MgSo$_4$, 0.05% Tris 1 M pH 7.5, 0.5% of 2% Gelatin) with a drop of chloroform and eluted by incubation at 37° C. for 20 minutes. The 2–11C lambda phage was subjected to secondary and tertiary screening to ensure purity. The 2–11C lambda phage stock was prepared by plating out method and stored at −70° C.

d. Restriction Enzyme Digestion Analysis of 2–11C lambda phage: The 2–11C phage DNA was digested with NotI, XbaI, XhoI and PstI restriction enzymes, gel fractionated on 0.8% agarose gel, transferred to nitrocellulose membrane (Molecular Cloning, Sambrook et al., 1989) and hybridized with DNA probe to putative bovine $D_H$ gene probe (pBF1H1 D3). Restriction digestion with PstI showed a 2.3 kB hybridizing band.

e. Subcloning of Approximately 2.3 kb Fragment of 2–11C Lambda Phage: The 2.3 kb fragment was blunt ended using T4 DNA polymerase (Pharmacia Amersham, Canada) followed by ligation into Zeroblunt Vector (Stratagene, USA) and transformation of *E. coli* 10 HB by electroporation (Gibco BRL, Canada). The transformed colonies were screened for recombinant plasmid by restriction digestion with EcoR1 and hybridization with the DNA probe (pBF1H1 D3) to putative bovine D-gene as described. This led to identification of pBGD14S recombinant plasmid (FIG. 2a (SEQ ID NOS:2–4) and 2b) that was subjected to automated DNA sequencing at the University of Guelph using M13 forward and M13 reverse primers.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Saini, S. S., Hein, W. and Kaushik, A. 1997. A single polymorphic immunoglobulin $V_H$ gene family related to mammalian group I, clan II, is identified in cattle. Molecular Immunology. 34:641–651.
2. Surinder Saini, PhD Thesis (1999). "Molecular immunogenetics of bovine antibody", University of Guelph, Guelph, Ontario, Canada.
3. Saini, S. S., Allore, B., Jacobs, R. M. and Kaushik, A. 1999. Exceptionally long CDR3H region with multiple cysteine residues in functional bovine IgM antibodies. Eur. J. Immunol. 29:2420–26.
4. Farbod Shojaei, MSc Thesis (2001). Molecular aspects of bovine DH genes. University of Guelph, Guelph.
5. Shojaei, F., Saini S. S., Kaushik A. K. 2003. Unusually long germline $D_H$ genes contribute to the generation of exceptionally long CDR3H in bovine antibodies. Molecular Immunology In press.

We claim:

1. An isolated bovine germline D-gene comprising:
   (a) the nucleic acid sequence as shown in SEQ ID NO:2, SEQ ID NO:3 or SEQ ID NO:4 wherein T can also be U; or
   (b) the nucleic acid sequence that is fully complementary to the nucleic acid sequence of (a).

2. An isolated bovine germline D-gene according to claim 1 comprising the nucleic acid sequence of D-1 (SEQ ID NO:2), D-2 (SEQ ID NO:3) and/or D-3 (SEQ ID NO:4).

3. An isolated bovine germline D-gene sequence comprising:
   (a) the nucleic acid sequence as shown in SEQ ID NO:6 wherein T can also be U; or
   (b) the nucleic acid sequence that is fully complementary to the nucleic acid sequence of (a).

4. An isolated bovine germline D sequence comprising the nucleic acid sequence of SEQ ID NO:6.

5. An isolated plasmid comprising the nucleic acid sequence of claim 1.

6. An isolated plasmid comprising the nucleic acid sequence of claim 3.

* * * * *